United States Patent [19]

Balde et al.

[11] 4,359,333

[45] Nov. 16, 1982

[54] PROCESS FOR THE HERBICIDAL TREATMENT OF SORGHUM USING 2,4-DIAMINO-6-CHLORO-5-METHYLTHIO-PYRIMIDINE

[75] Inventors: Daniel H. Balde, Paris; Gerard E. M. Boutemy, Milly la Foret, both of France

[73] Assignee: Produits Chimiques Ugine Kuhlmann, Courbevoie, France

[21] Appl. No.: 121,613

[22] Filed: Feb. 14, 1980

[30] Foreign Application Priority Data

Feb. 23, 1979 [FR] France .................. 79 4635

[51] Int. Cl.³ ............... A01N 43/48; A01N 43/64
[52] U.S. Cl. ........................... 71/92; 71/93; 71/118
[58] Field of Search ........................... 71/92

[56] References Cited

U.S. PATENT DOCUMENTS 4,082,535  4/1978  Hoegerle et al. ............... 71/92

FOREIGN PATENT DOCUMENTS 6681  7/1978  European Pat. Off. ............... 71/92

OTHER PUBLICATIONS

Costes, "Photosyntheses et Production, etc;", Formation Permanente en Ecologie et Biol., pp. 90–91, (1975).
Ellis, et al., "Effectiveness of a New Sofener etc;" (1980), Weed Sci. 28, pp. 1–5.
Leopold, et al., "Plant Growth & Development", McGraw-Hill Book Co., 2nd Ed., pp. 68, 69 & 428, (1975).
Komoto, et al., "6-Chloro-2,4-diamino, etc;" (1978), (also translation) CA 90 No. 54968y, (1979).
Mossini, et al., "Studies on the Phytocidal, etc;" (1978), (also orig. art.), CA 89 No. 101721d. (1978).

*Primary Examiner*—Glennon H. Hollrah
*Attorney, Agent, or Firm*—Beveridge, DeGrandi and Kline

[57] ABSTRACT

A process for destroying weeds in sorghum crops which comprises applying to the area of the growing crop or to the crop area before the crop emerges, 2,4-diamino-6-chloro-5-methylthio-pyrimidine or a mixture of the two isomeric compounds 2,4-diamino-6-chloro-5-methylthio-pyrimidine and 4,6-diamino-2-chloro-5-methylthio-pyrimidine in which 2,4-diamino-6-chloro-5-methylthio-pyrimidine is preponderant, the rate of application of the above compound or mixture being from 300 g/ha to 4,500 g/ha. Herbicides may be simultaneously applied.

1 Claim, No Drawings

PROCESS FOR THE HERBICIDAL TREATMENT OF SORGHUM USING 2,4-DIAMINO-6-CHLORO-5-METHYLTHIO-PYRIMIDINE

The present invention relates to a process for destroying weeds in sorghum crops, in which the herbicidal agent used is 2,4-diamino-6-chloro-5-methylthio-pyrimidine (compound hereinafter referred to as A) or a mixture of the two isomeric compounds 2,4-diamino-6-chloro-5-methylthio-pyrimidine (compound A) and 4,6-diamino-2-chloro-5-methylthio-pyrimidine (compound B) in which compound A is preponderant, that is to say the percentage by weight of A in the mixture is at least 50% and preferably at least 80%.

Compounds A and B and their mixtures are known products which are described in European patent application No. 78400062.2 (publication No. 681) and in Japanese patent application No. 77/6,335 (publication No. 78/92,789). None of these documents decribes the use of said products in a process for the herbicidal treatment of sorghum.

The process according to the invention comprises applying to the area of the growing crop (post-emergence application) or to the crop area before the crop emerges (pre-emergence application) compound A or a mixture of compounds A and B wherein compound A is preponderant, the dose of compound A or of the mixture of A and B used ranging from 300 g/ha to 4,500 g/ha, preferably from 600 g/ha to 3,000 g/ha. In the pre-emergence application there may simultaneously be applied a herbicide belonging to the triazine family (atrazine, cyanazine, simazine, terbutryne, etc.), the dose of such herbicide used ranging from 500 g/ha to 5,000 g/ha. In the post-emergence application there may simultaneously be applied a herbicide chosen from atrazine, simazine and the family of acetanilides, in particular alachlor and propachlor, the dose of such herbicide used ranging from 500 g/ha to 5,000 g/ha.

The herbicidal compounds used in the process of the invention are preferably applied in the form of a composition which contains, in addition to the active material (that is, compound A or the mixture of compounds A and B, and possibly one of the herbicides indicated above), inert additives normally used in agriculture to dilute the active materials and to facilitate putting in aqueous suspension, adherence to foliage and resistance to atmospheric agents and to biological degradations. Such inert additives are well known by one of ordinary skill in the art. As such may be mentioned solid diluents (talc, silica, kieselguhr, chalk, diatomaceous earth, clay, etc.), liquid diluents (water, mineral oils, organic solvents), anionic or non-ionic surface-active substances, dispersants, adjuvants, and wetting agents.

The compositions in which the active material is incorporated are prepared by intimately mixing suitable amounts of the various constituents. Such compositions may be particularly in the form of wettable powders or in the form of stable aqueous suspensions. These suspensions are applied by spraying on the area of the growing sorghum crops or on the crops area, before the crops emerge.

The process according to the present invention enables a large number of undesirable plants to be destroyed belonging to the monocotyledon or dicotyledon classes, especially panicum milliaceum, and this without disturbing the development of the cultivated plant.

The following examples illustrate the invention without it being restricted thereto. In the examples and throughout the specification and claims, all parts and percentages are by weight unless otherwise specified.

EXAMPLE 1

The object of this test is to demonstrate the absence of phytotoxicity of the active material towards sorghum.

The active material is a mixture containing approximately 89% by weight of compound A and 11% by weight of compound B. It is incorporated in a wettable powder having the following composition (the percentages are by weight):
- 80% of active material
- 10% of talc
- 6% of silica
- 3% of sodium methylnaphthalenesulfonate (dispersant)
- 1% of the polyethoxyether of fatty alcohol known by the trademark REMCOPAL L02B (non-ionic adhesive agent).

The wettable powder is diluted in water before use and the suspenson thus obtained is sprayed, at the rate of 1,000 l/ha, on sorghum plants (NK 121 variety) at the three leaves stage, which are grown in a greenhouse. The dilutions are calculated to give the doses of active material indicated in the following Table 1.

15 days, then 30 days after the application of the suspensions, the degree of phytotoxicity towards the cultivated plant is evaluated. This degree of phytotoxicity is expressed by a value from 0 to 10. 0 corresponds to an undamaged plant and 10 to a destroyed plant. The results obtained are summarized in the following Table 1:

TABLE 1

| Active material | Dose of active material applied (g/ha) | Degree of phytotoxicity towards the sorghum | |
|---|---|---|---|
| | | 15 days | 30 days |
| Mixture 89% of A + 11% of B | 625 | 0 | 0 |
| Mixture 89% of A + 11% of B | 1,250 | 0.5 | 0 |
| Mixture 89% of A + 11% of B | 2,500 | 1 | 0 |

EXAMPLE 2

Herbicidal Treatment of Sorghum (Post-emergence Application)

The active material (mixture A+B of Example 1) is formulated as indicated in Example 1. The wettable powder is diluted in water before use and the suspension obtained is sprayed, at the rate of 1,000 liters/ha, on sorghum plants (NK 121 variety) in small plots, at the six leaves stage, which are infested with various gramineous or dicotyledonous adventitious plants (panicum milliaceum, setaria sp., chenopodium sp., etc.). The dilutions are calculated to give the doses of active material indicated in the following Tables 2 and 3.

30 days, 60 days and 90 days after the application of the suspensions, the herbicidal efficiency towards the adventitious plants is evaluated on the one hand and on the other hand the degree of phytotoxicity towards the cultivated plant is estimated. The herbicidal efficiency is expressed by the percentage of destruction of the adventitious plants, the index 0 being assigned by convention to the untreated control and the index 100 corresponding to a total destruction of the adventitious plants. The degree of phytotoxicity towards the cultivated plant is expressed by a value from 0 to 10, 0 corresponding to an undamaged plant and 10 to a destroyed plant.

The results obtained are summarized in the following Tables 2 and 3.

TABLE 2

| Active material | Dose of active material applied (g/ha) | Degree of phytotoxicity towards the sorghum | | |
|---|---|---|---|---|
| | | 30 days | 60 days | 90 days |
| Mixture of A + B of Example 1 | 1,200 | 0 | 0 | 0 |
| Mixture of A + B of Example 1 | 2,400 | 1 | 0 | 0 |
| Mixture of A + B of Example 1 | 3,600 | 1.5 | 0 | 0 |

TABLE 3

| Active material | Dose of active material applied (g/ha) | Herbicidal efficiency towards the adventitious plants | | |
|---|---|---|---|---|
| | | 30 days | 60 days | 90 days |
| Mixture of A + B of Example 1 | 1,200 | 80 | 75 | 65 |
| Mixture of A + B of Example 1 | 2,400 | 100 | 100 | 100 |
| Mixture of A + B of Example 1 | 3,600 | 100 | 100 | 100 |

Other suitable herbicides belonging to the family of acetanilides which may be used include metolachlor.

What is claimed is:

1. A process for destroying weeds in sorghum crops which comprises applying to the area of the growing crop a mixture containing approximately 89% by weight of 2,4-diamino-6-chloro-5-methylthio-pyrimidine and 11% by weight of 4,6-diamino-2-chloro-5-methylthio-pyrimidine, the rate of application of the above mixture being from 1,200 g/ha to 3,600 g/ha.

* * * * *